United States Patent
Lozano

(10) Patent No.: US 12,194,133 B2
(45) Date of Patent: *Jan. 14, 2025

(54) COMPOSITION AND METHOD FOR PROMOTING HAIR GROWTH

(71) Applicant: Hilda L. Lozano, El Paso, TX (US)

(72) Inventor: Hilda L. Lozano, El Paso, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/406,034

(22) Filed: Aug. 18, 2021

(65) Prior Publication Data

US 2023/0053978 A1    Feb. 23, 2023

(51) Int. Cl.
*A61K 8/92* (2006.01)
*A61K 8/9789* (2017.01)
*A61Q 7/00* (2006.01)

(52) U.S. Cl.
CPC ............ *A61K 8/922* (2013.01); *A61K 8/9789* (2017.08); *A61Q 7/00* (2013.01); *A61K 2800/5922* (2013.01); *A61K 2800/805* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2009/0068128 A1* | 3/2009 | Waddington | A61K 8/9789 424/59 |
| 2010/0322887 A1* | 12/2010 | Aoki | A61K 8/55 558/162 |
| 2021/0401719 A1* | 12/2021 | Naiberk | A61K 8/732 |

OTHER PUBLICATIONS

Amy, How to Make Homemade Hot Oil Hair Treatment, retrieved from URL :<http://utry.it/2013/09/how-to-make-homemade-hot-oil-hair.html>, Sep. 21, 2013. (Year: 2013).*

* cited by examiner

*Primary Examiner* — Nannette Holloman
(74) *Attorney, Agent, or Firm* — Lewis Roca Rothgerber Christie LLP

(57) ABSTRACT

A method and composition for promoting hair growth comprises an oil solution created with predetermined quantities of certain oils such as sesame oil, avocado oil, sweet almond oil, coconut oil, and ricinus oil. A blended final product is created by adding predetermined quantities of certain plants to the oil solution, such as parsley and aloe vera. The final product is heated and applied to a surface for hair growth. After a certain amount of time it is washed off the surface for hair growth. These steps are repeated daily for a full course of treatment, which comprises a few weeks. The course may be repeated about every other month.

19 Claims, 1 Drawing Sheet

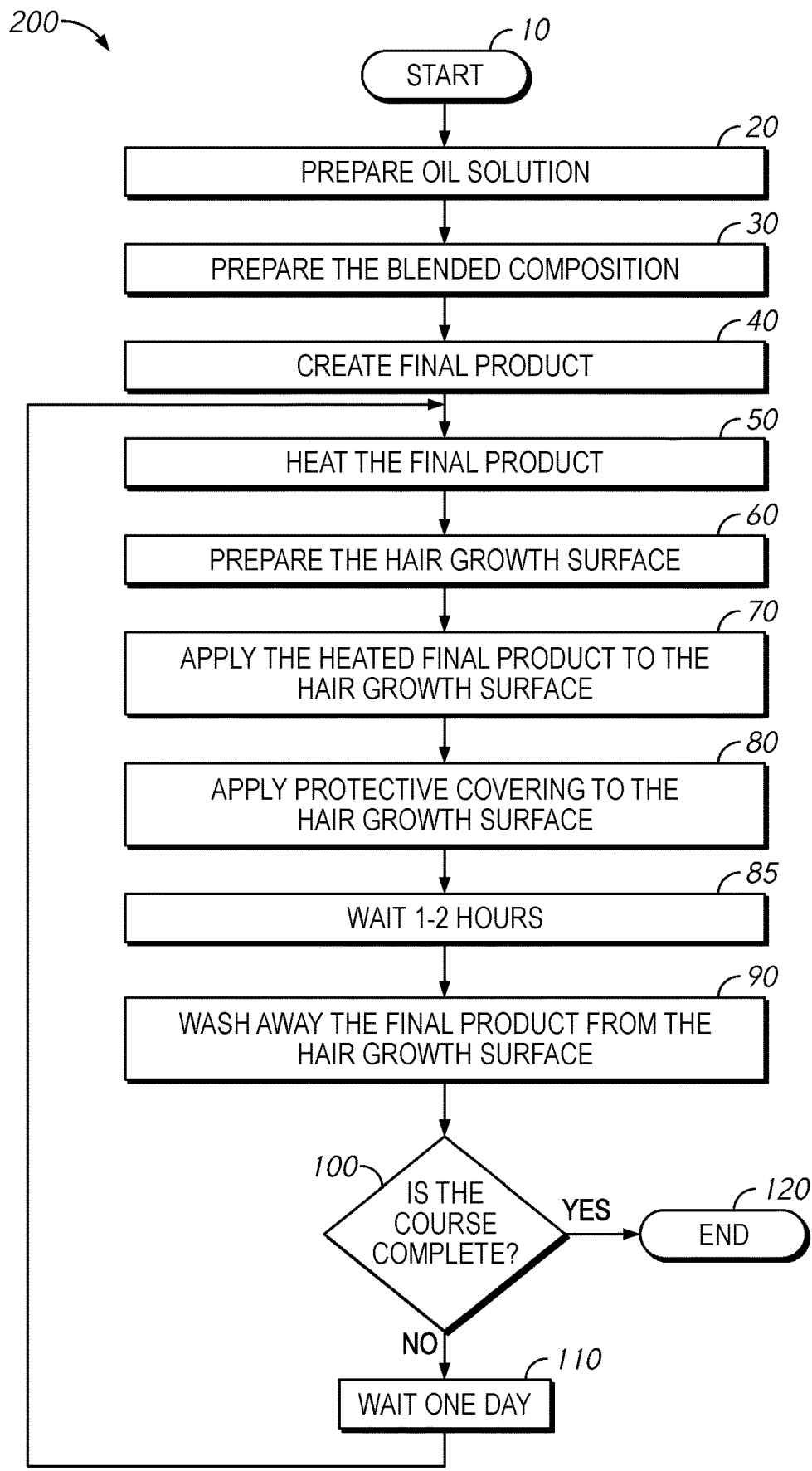

COMPOSITION AND METHOD FOR PROMOTING HAIR GROWTH

FIELD OF INVENTION

This invention concerns hair, and more specifically, to a composition and method for promoting the growth of hair.

BACKGROUND

A considerable portion of the general human population suffers from unwanted hair loss. The condition is often marked by a slow loss of hair over time, which becomes more pronounced during the latter years of a person's life. This results in a thinning of the person's hair, which is undesirable because it is aesthetically less appealing.

Sometimes other factors may cause hair loss. Cancer patients may experience a loss of hair due to chemotherapy treatment, or some patients may suffer from alopecia areata. Or a person may be genetically predisposed to hair loss with age, such as male pattern baldness. Some patients may suffer from trichotillomania, or an autoimmune disease, or the like, that causes hair loss. But irrespective of the actual reasons causing the person's hair loss, it is usually desirable to regrow hair that has been lost.

Some products and methods are available commercially to help regrow lost hair. Many of those products or methods are generally ineffective, or weak in their effectiveness. Some of the more effective treatments are expensive and may not be easily affordable by the average patient. Other treatments fall under regulation by the U.S. Food and Drug Administration, which causes the treatment to be more expensive and require a formal prescription from a doctor to obtain the product. Such process adds to the time and inconvenience for patients needing the treatment. Such additional expense, along with the added inconvenience, are generally undesirable. Further, some of those products have to be ingested, which raises additional concerns of side effects and potential harm to the patient's body, especially if used over a longer period of time.

Accordingly, there is a need for a product which is effective for the growth of hair, which is used externally whereby a patient does not need to ingest anything, and which is safe for over-the-counter sales to the general population. It is also desirable for the product to be cost-effective for the average patient.

COPYRIGHT NOTICE

© 2021 Hilda L. Lozano. The disclosure in this patent document includes material that is subject to copyright protection. The copyright owner consents to fair use by facsimile reproduction of the patent document or of the patent disclosure as it appears in the U.S. Patent and Trademark Office's records. Apart from that, all copyright rights to the disclosure herein are expressly reserved. 37 CFR § 1.71(d).

SUMMARY OF THE INVENTION

An oil solution is prepared, comprising certain predetermined oils. In one embodiment, the oil solution comprises about 2.5% to 3.1% sesame oil, about 2.5% to 3.1% avocado oil, about 30% to 36% sweet almond oil, about 14% to 19% coconut oil, and about 40% to 48% of ricinus oil. The oil solution is created by mixing these oils together.

A blended composition is prepared by adding two plants to the oil solution. The first plant is parsley, about five (5) stems of parsley are added for each 8 oz, or half-pound (lb), of the oil solution. The second plant is aloe vera, about twelve inches (12") of aloe vera are added for each 8 oz, or half-pound (lb), of the oil solution.

The oil solution with the two plants added to it is then blended together. This prepares the blended composition.

The final product is created by mixing approximately equal amounts of the blended composition and the oil solution. The final product is then heated.

A hair-growth surface is washed and prepared for application of the final product. The hair-growth surface will typically be the scalp of the patient. The heated final product is applied to the hair-growth surface.

The heated final product stays on the hair-growth surface in substantial part, and does not run. This is achieved, for example, by applying a protective covering on the hair-growth surface.

The warm final product is maintained on the hair-growth surface in this manner for about one (1) to two (2) hours. After the one (1) to two (2) hour time period has elapsed, the warm final product is rinsed and washed off from the hair-growth surface.

These steps are repeated daily, once per day, for a pre-determined number of days that comprise a full course of treatment. In one embodiment, the duration of a full course is about five to six weeks, where these steps are repeated daily, five days a week, for about five to six weeks.

The patient may repeat a course about every other month, or as desired by the patient.

BRIEF DESCRIPTION OF THE FIGURES

The invention can be better understood with reference to the figures. In these figures, like reference numerals designate corresponding parts throughout the different figures and views.

FIG. 1 shows a flowchart of the method of practicing one embodiment of the present invention.

DETAILED DESCRIPTION

The systems, methods, and apparatus of the present invention are described below with reference to the figures. The description and figures are for illustrative purposes only, they do not limit the true scope and spirit of the present invention. The true scope and spirit of the present invention is evidenced by all parts of the disclosure herein, including but not limited to the Summary, the Figures, the Detailed Description, the Abstract, and the Claims, along with equivalents thereof.

Referring to FIG. 1, flowchart 200 shows a method of practicing one embodiment of the present invention. The method starts 10 with obtaining all the materials and apparatus needed to practice the present invention. The needed materials and apparatus are discussed in more detail below.

An oil solution must be prepared 20 first. In one embodiment, the oil solution comprises certain predetermined oils, each in predetermined quantities, mixed together. Depending on the overall quantity, or size, of the particular batch of the oil solution being prepared, the quantities of each oil therein can be described in terms of its percentage composition of the overall oil solution. Additionally, the specific measured quantity of each oil can be provided in ounces for purposes of an exemplary batch of the oil solution.

In one embodiment, the oil solution comprises about 2.8% sesame oil. For purposes of an exemplary batch, that translates to about 0.5 ounce. To provide a range of the composition of sesame oil in the oil solution, sesame oil preferably comprises about 2.5% to 3.1% of the oil solution. Sesame oil is a commonly known product, it is available commercially over the counter.

In one embodiment, the oil solution comprises about 2.8% avocado oil. In the exemplary batch, that translates to about 0.5 ounce. To provide a range of the composition of avocado oil in the oil solution, avocado oil preferably comprises about 2.5% to 3.1% of the oil solution. Avocado oil is a commonly known product, it is available commercially over the counter.

In one embodiment, the oil solution comprises about 33.3% sweet almond oil. In the exemplary batch, that translates to about six (6) ounces. To provide a range of the composition of sweet almond oil in the oil solution, sweet almond oil preferably comprises about 30% to 36% of the oil solution. Sweet almond oil is a commonly known product, it is available commercially over the counter.

In one embodiment, the oil solution comprises about 16.7% coconut oil. In the exemplary batch, that translates to about three (3) ounces. To provide a range of the composition of coconut oil in the oil solution, coconut oil preferably comprises about 14% to 19% of the oil solution. Coconut oil is a commonly known product, it is available commercially over the counter.

In one embodiment, the oil solution comprises about 44.4% ricinus oil. In the exemplary batch, that translates to about eight (8) ounces. To provide a range of the composition of ricinus oil in the oil solution, ricinus oil preferably comprises about 40% to 48% of the oil solution. Ricinus oil is derived from cold pressing the seeds of the *Ricinus communis* plant. It is available commercially. It is sometimes confused in the industry with castor oil, because both are derived from the *Ricinus communis* plant. However, the present invention utilizes ricinus oil.

The oil solution is created 20 by mixing the above oils together.

The next step is to prepare the blended composition 30. To prepare the blended composition 30, two plants are added to the oil solution. The first plant is parsley. Approximately five (5) stems of parsley are added for each 8 oz, or half-pound (lb), of the oil solution. Parsley is commonly available in grocery stores.

The second plant is aloe vera. About twelve inches (12") of aloe vera are added for each 8 oz, or half-pound (lb), of the oil solution. In one embodiment, two pieces of aloe vera, about six inches (6") each in length, for a total of twelve inches (12") are added for each 8 oz, or half-pound (lb), of the oil solution. Aloe vera is a cactus-like plant that grows in hot and dry climates. It comprises elongated stems, which are sometimes cultivated for different uses. Aloe vera is commercially available for purchase.

The oil solution with the two plants added to it is then blended together. They are blended together at least until the plants are in a liquefied state. The result is a fairly uniform blended mixture. This completes the step of preparing the blended composition 30.

The next step is to create the final product 40. The final product is created by mixing approximately equal amounts of the blended composition and the oil solution. In one embodiment, about three (3) ounces of the blended composition are mixed with about three (3) ounces of the oil solution, creating the final product.

The next step is to gently heat the final product 50. In the preferred embodiment, water is heated and the final product is placed in a spray bottle, in a pot, or in a waterproof bag, or in a pouch, or the like, and placed in the heated water. The water is preferably not heated all the way up to the boiling point. Placing the final product in the heated water warms the final product, and the final product reaches a lukewarm temperature in one embodiment. A user may test the temperature by hand or on their skin, for example, to verify that the final product has reached a lukewarm temperature.

Alternatively, the final product may be warmed by another method or process, provided that the warming process is gentle and does not damage the final product. However, in the preferred embodiment the final product is not heated directly or in a microwave oven. That is because certain desired properties of the final product may be adversely impacted.

The next step comprises preparing the hair-growth surface 60 for application of the final product. The hair-growth surface will typically be the scalp of the patient. The surface is prepared by washing and cleaning the area, including washing any other hair on the hair-growth surface. For example, hair on the hair-growth surface may be shampooed and washed. But the hair-growth surface must be washed clean, such as with clean water, and be free of any residue from soap, shampoo, etc. After it has been washed and cleaned, any preexisting hair on the hair-growth surface may be brushed.

The next step comprises applying the heated final product to the hair-growth surface 70. The patient may apply a generous amount to the hair growth surface, such as one to two tablespoons to a scalp. In one embodiment, the patient applies a few ounces of the warm final product to his scalp.

In the preferred embodiment, the heated final product stays on the hair-growth surface in substantial part, and does not run. This can be achieved by applying a protective covering on the hair-growth surface 80. In one embodiment, a shower cap is placed on the scalp, which helps entrap the warm final product on the scalp. This prevents wastage of the warmed final product, and its efficacy on the hair-growth surface is maximized.

Further, as an optional step, a cover may be placed atop the protective covering. In one embodiment, a towel is placed on top of the shower cap.

The warm final product is preferably maintained on the hair-growth surface in this manner for about one (1) to two (2) hours 85. The warm final product is preferably maintained undisturbed in this manner for that duration of time.

After the one (1) to two (2) hour time period has elapsed in this state, the warm final product may be rinsed and washed off from the hair-growth surface 90. This is typically done with clean water. The goal is to completely rinse clean the hair-growth surface so that no residue from the warm final product remains.

Steps 10 through 90 are preferably repeated daily 100, once per day, for a predetermined number of days that comprise a full course of treatment. In one embodiment, the duration of a full course of treatment is about five to six weeks, where these steps are repeated daily for five days per week for about five to six weeks. If the course is not complete 100, then the patient must wait a day 110 and repeat steps 10 through 90 the following day. Otherwise, if the course is complete, then the patient is done 120 with that course.

For the patient's very first course of treatment, the course will typically be longer. In one embodiment, the patient's first course lasts about two to three months. The subsequent courses may then be shorter, about five to six weeks.

It is anticipated that some of the oil solution and the blended composition may be left over and used over the following days. In that regard, steps 20 and 30 may be skipped if there is an available inventory of a previous preparation of the oil solution and the blended composition. However, the final product must be refrigerated. Even refrigerated, the final product's expected shelf-life will only be about 15 days. After that time any left-over amount of the final product must be discarded. For example, if the final product is put in a spray bottle, the spray bottle must be kept refrigerated and the final product therein may be reused daily for a maximum period of about 15 days. After that time the patient must discard any remaining final product and create a new batch of final product for completing the patient's current course of treatment.

In one embodiment, the patient may repeat a course about every other month. This will be helpful if the patient desires more optimum results from practicing the present invention. Although the repeated course does not have to be a full course of five to six weeks, the repeat course may be anywhere between one (1) to three (3) weeks, and will typically depend on the amount of hair growth that is desired.

Although the apparatus and methods have been described and illustrated in connection with certain embodiments, variations and modifications will be evident to those skilled in the art. Such variations and modifications may be made without departing from the scope and spirit of the present disclosure, and are therefore anticipated. The description and teachings herein are thus not to be limited to the precise details of methodology or construction set forth herein because variations and modification are intended to be included within the scope and spirit of the present disclosures and teachings.

I claim:

1. A method to promote hair growth, comprising:
   preparing an oil solution, said oil solution comprising sesame oil, avocado oil, sweet almond oil, coconut oil, and ricinus oil;
   preparing a blended composition, said blended composition comprising said oil solution, parsley, and aloe vera;
   creating a final product, said final product created by mixing equal quantities of said oil solution and said blended composition;
   heating said final product; and
   applying said final product to a surface for hair growth.

2. The method of claim 1, wherein said oil solution comprises:
   2.5% to 3.1% sesame oil; and
   2.5% to 3.1% avocado oil.

3. The method of claim 1, wherein said oil solution comprises:
   about 30% to 36% sweet almond oil; and
   about 14% to 19% coconut oil.

4. The method of claim 1, wherein said oil solution comprises 40% to 48% ricinus oil.

5. The method of claim 1, wherein said blended composition comprises about five stems of parsley per 8 oz of said oil solution.

6. The method of claim 1, wherein said blended composition comprises about twelve inches of aloe vera per 8 oz of said oil solution.

7. The method of claim 1, wherein said final product is applied to a surface for hair growth once per day, five days per week, for five to six weeks.

8. The method of claim 1, further comprising covering said surface for hair growth with a protective covering after said final product is applied to said surface for hair growth.

9. The method of claim 1, wherein heating the final product comprises:
   heating water; and
   placing said final product in a container; and
   putting said container in said heated water.

10. The method of claim 1, wherein said oil solution comprises about 2.8% sesame oil, about 2.8% avocado oil, about 33.3% sweet almond oil, about 16.7% coconut oil, and about 44.4% ricinus oil.

11. The method of claim 1, further comprising:
    waiting one to two hours after said final product is applied to said surface for hair growth, and
    rinsing the final product off of said surface for hair growth.

12. A composition for hair growth, comprising:
    an oil solution, said oil solution comprising:
       2.5% to 3.1% sesame oil,
       2.5% to 3.1% avocado oil,
       30% to 36% sweet almond oil,
       14% to 19% coconut oil, and
       40% to 48% ricinus oil; and
    said oil solution mixed with:
       about five stems of parsley per 8 oz of said oil solution, and
       about twelve inches of aloe vera per 8 oz of said oil solution.

13. The composition of claim 12, wherein said oil solution mixed with parsley and aloe vera is blended together.

14. The composition of claim 13, further comprising about an equal amount of said oil solution mixed with an equal amount of said blend of said oil solution and said parsley and aloe vera.

15. The composition of claim 12, wherein said oil solution comprises about 2.8% sesame oil.

16. The composition of claim 12, wherein said oil solution comprises about 2.8% avocado oil.

17. The composition of claim 12, wherein said oil solution comprises about 33.3% sweet almond oil.

18. The composition of claim 12, wherein said oil solution comprises about 16.7% coconut oil.

19. The composition of claim 12, wherein said oil solution comprises about 44.4% ricinus oil.

* * * * *